(12) United States Patent
Ziero et al.

(10) Patent No.: US 12,128,208 B2
(45) Date of Patent: Oct. 29, 2024

(54) MODULAR UNIT FOR WASHING AND DRYING CONTAINERS FOR PHARMACEUTICAL USE AND PRODUCTION LINE OF CONTAINERS FOR PHARMACEUTICAL USE DESCRIPTION

(71) Applicant: Stevanato Group S.P.A., Piombino Dese (IT)

(72) Inventors: Paolo Ziero, Piombino Dese (IT); Fabio Perin, Vedelago (IT)

(73) Assignee: STEVANTO GROUP S.P.A., Piombino Dese (IT)

( * ) Notice: Subject to any disclaimer, the term of this patent is extended or adjusted under 35 U.S.C. 154(b) by 357 days.

(21) Appl. No.: 17/664,061

(22) Filed: May 19, 2022

(65) Prior Publication Data
US 2022/0379005 A1    Dec. 1, 2022

(30) Foreign Application Priority Data
May 19, 2021 (IT) .................. 102021000012950

(51) Int. Cl.
| | | |
|---|---|---|
| *A61M 5/00* | (2006.01) | |
| *B08B 3/02* | (2006.01) | |
| *B08B 9/08* | (2006.01) | |
| *B08B 9/093* | (2006.01) | |
| *B08B 9/20* | (2006.01) | |
| *B08B 9/32* | (2006.01) | |
| *B08B 9/42* | (2006.01) | |

(52) U.S. Cl.
CPC ............ *A61M 5/001* (2013.01); *B08B 3/022* (2013.01); *B08B 9/0813* (2013.01); *B08B 9/0826* (2013.01); *B08B 9/093* (2013.01); *B08B 9/205* (2013.01); *B08B 9/32* (2013.01); *B08B 9/426* (2013.01)

(58) Field of Classification Search
CPC .................................................... A61M 5/001
See application file for complete search history.

(56) References Cited

FOREIGN PATENT DOCUMENTS

| | | |
|---|---|---|
| CN | 110216121 A | 9/2019 |
| DE | 19517998 A1 | 11/1996 |
| DE | 102009021137 A1 | 12/2009 |
| EP | 0634230 A1 | 1/1995 |
| EP | 1363096 A1 | 11/2003 |
| EP | 1885514 A2 | 2/2008 |
| EP | 3085629 A1 | 10/2016 |
| EP | 3741474 A1 | 11/2020 |
| EP | 3747561 A1 | 12/2020 |
| WO | 0038851 A1 | 7/2000 |

*Primary Examiner* — Jason Y Ko

(57) ABSTRACT

A modular unit for washing and drying containers for pharmaceutical use includes a load transfer unit configured to take a plurality of containers for pharmaceutical use from an associated input transfer unit, a washing tower, a group of grippers configured to take said containers for pharmaceutical use from the load transfer unit and loading them onto said washing tower, at least one washing station, at least one drying station and at least one unloading station for said containers for pharmaceutical use. The washing tower is configured to move the containers for pharmaceutical use through said washing stations, drying stations and unloading stations. The drying station includes at least one lower drying nozzle configured to direct a flow of air from the bottom to the top inside the containers and at least one upper drying nozzle configured to blow air from above.

15 Claims, 8 Drawing Sheets

MODULAR UNIT FOR WASHING AND DRYING CONTAINERS FOR PHARMACEUTICAL USE AND PRODUCTION LINE OF CONTAINERS FOR PHARMACEUTICAL USE DESCRIPTION

CROSS REFERENCES

This application claims priority to Italian Application No. 102021000012950 filed on May 19, 2021, the disclosure of which is expressly incorporated by reference herein in its entirety.

TECHNICAL FIELD

The present invention relates to a modular unit for washing and drying containers for pharmaceutical use and to a production line of containers for pharmaceutical use comprising said modular unit.

BACKGROUND

As is well known, in the pharmaceutical sector there is a need to wash containers, such as syringes, carpules, capsules and the like, before filling, loading and/or packaging them.

The known solutions involve complex and costly production lines, for example of syringes, which comprise, among other production stations, specific washing stations for said containers for pharmaceutical use.

Therefore, the known solutions are rigid and inflexible, as they involve the implementation of specific production lines which include, along the various stations, specific washing stations.

SUMMARY OF THE DISCLOSURE

There is thus a need to overcome the inconveniences and limitations mentioned with reference to the prior art.

Such a need is met by a modular unit for washing and drying containers for pharmaceutical use according to claim 1.

BRIEF DESCRIPTION OF THE DRAWINGS

Further features and advantages of the present invention will be more readily understood from the following description of its preferred and non-limiting examples of embodiments, in which.

Figure 1:
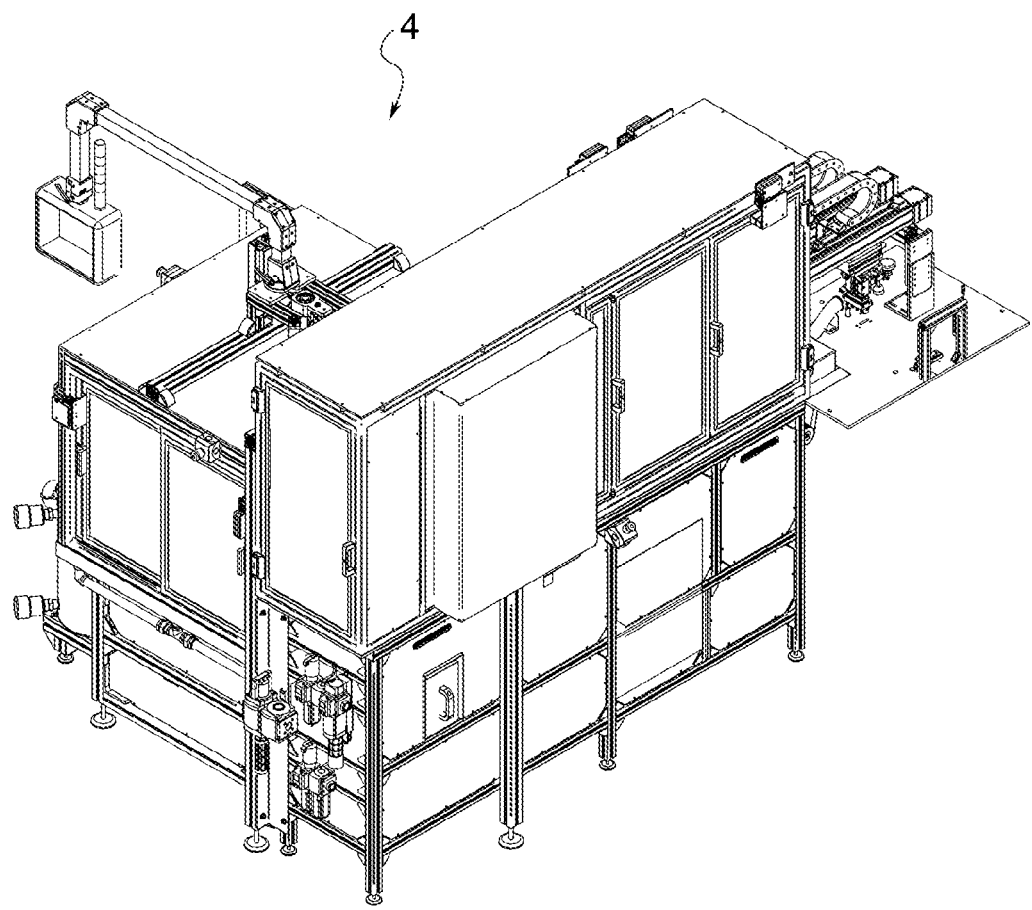
FIG. 1 depicts a perspective view of a modular unit in accordance with an embodiment of the present invention.
Figure 2:
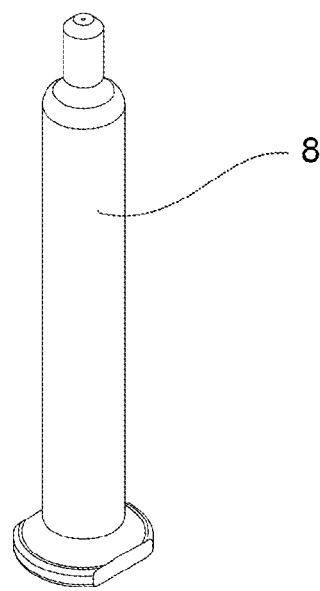
FIG. 2 depicts a perspective view of a possible container for pharmaceutical use suitable for being treated by the modular unit in accordance with the present invention.
Figure 3:
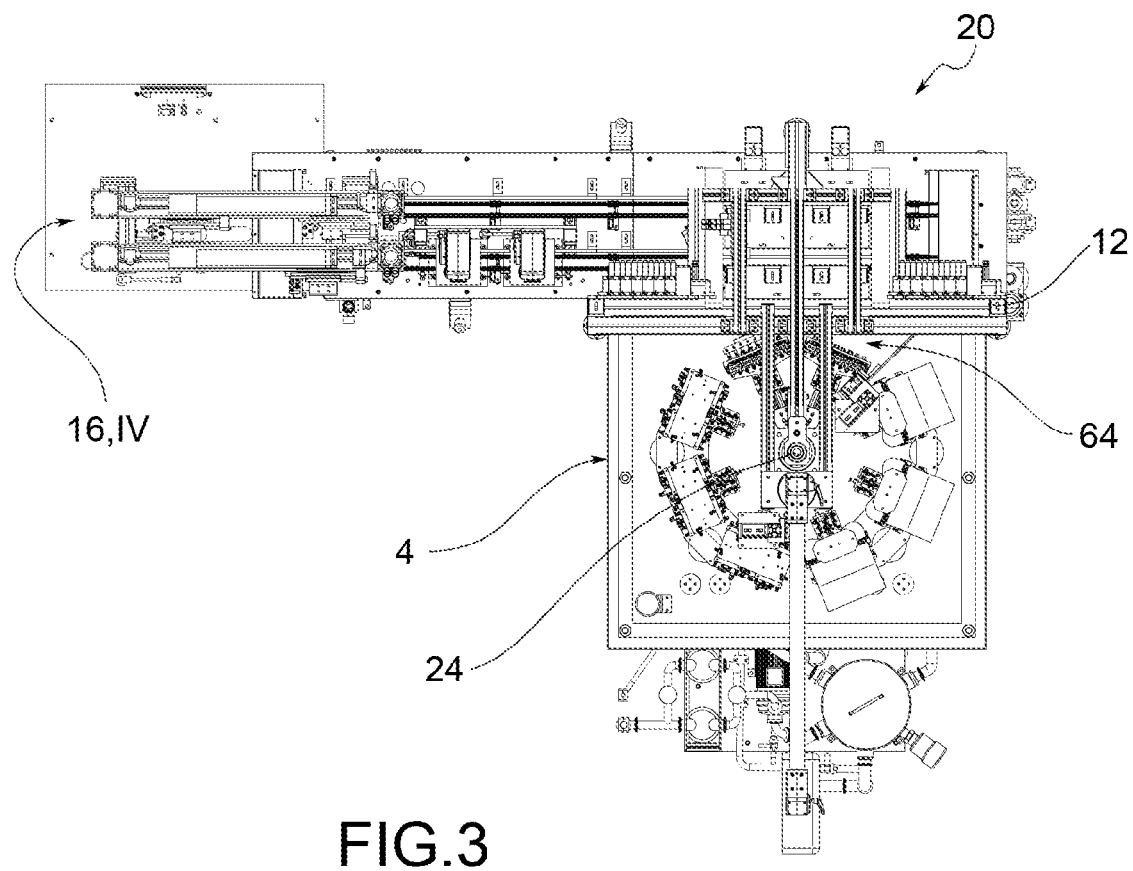
FIG. 3 depicts a plan view of a production line comprising a modular unit according to the present invention.
Figure 4:
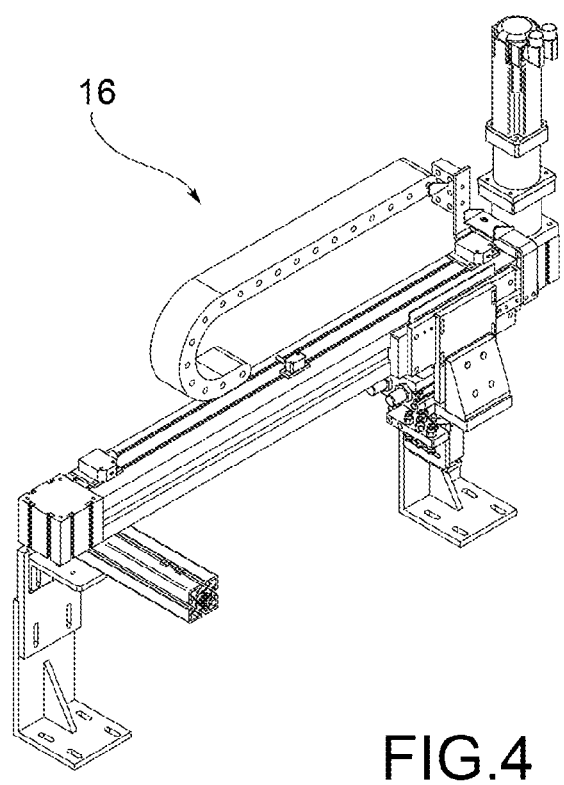
FIG. 4 depicts the enlarged detail IV shown in FIG. 3.
Figure 5:
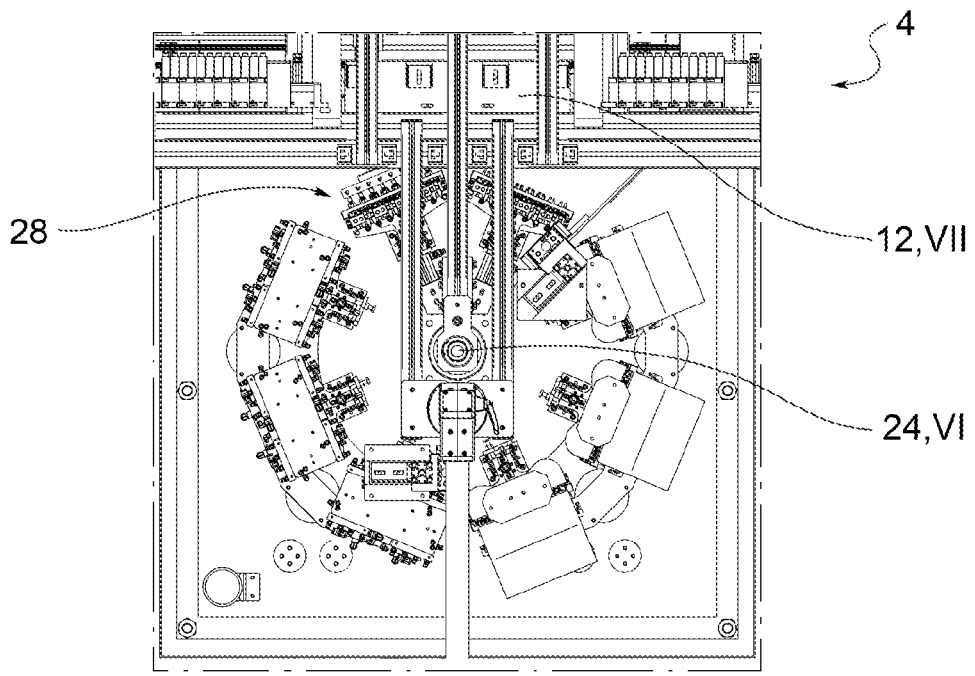
FIG. 5 depicts a plan view of the modular unit in accordance with an embodiment of the present invention.
Figure 6:
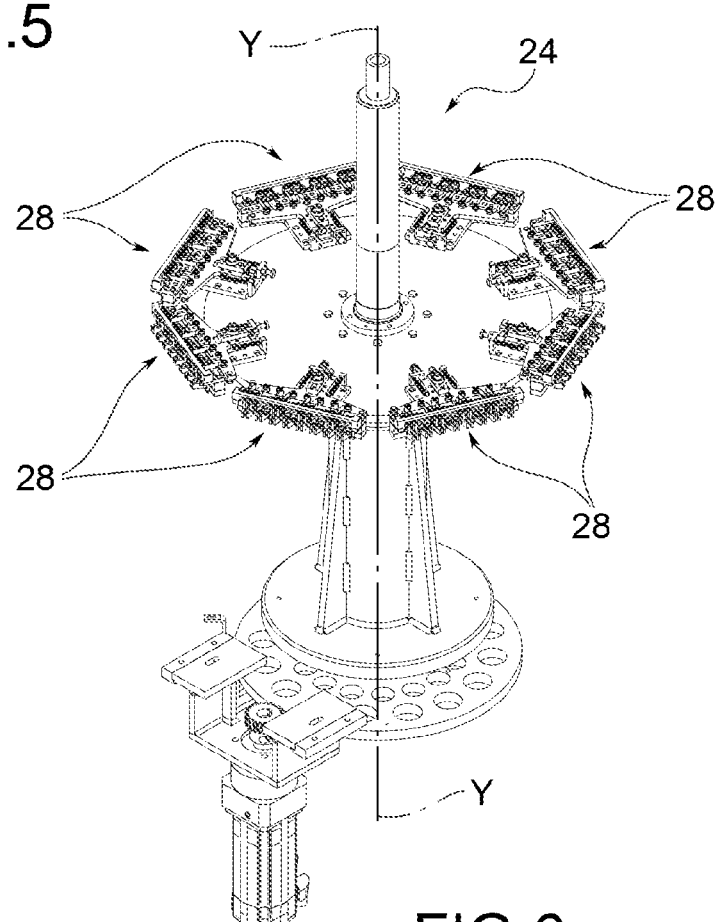
FIG. 6 depicts a perspective view of the enlarged detail VI, shown in FIG. 5.
Figure 7:
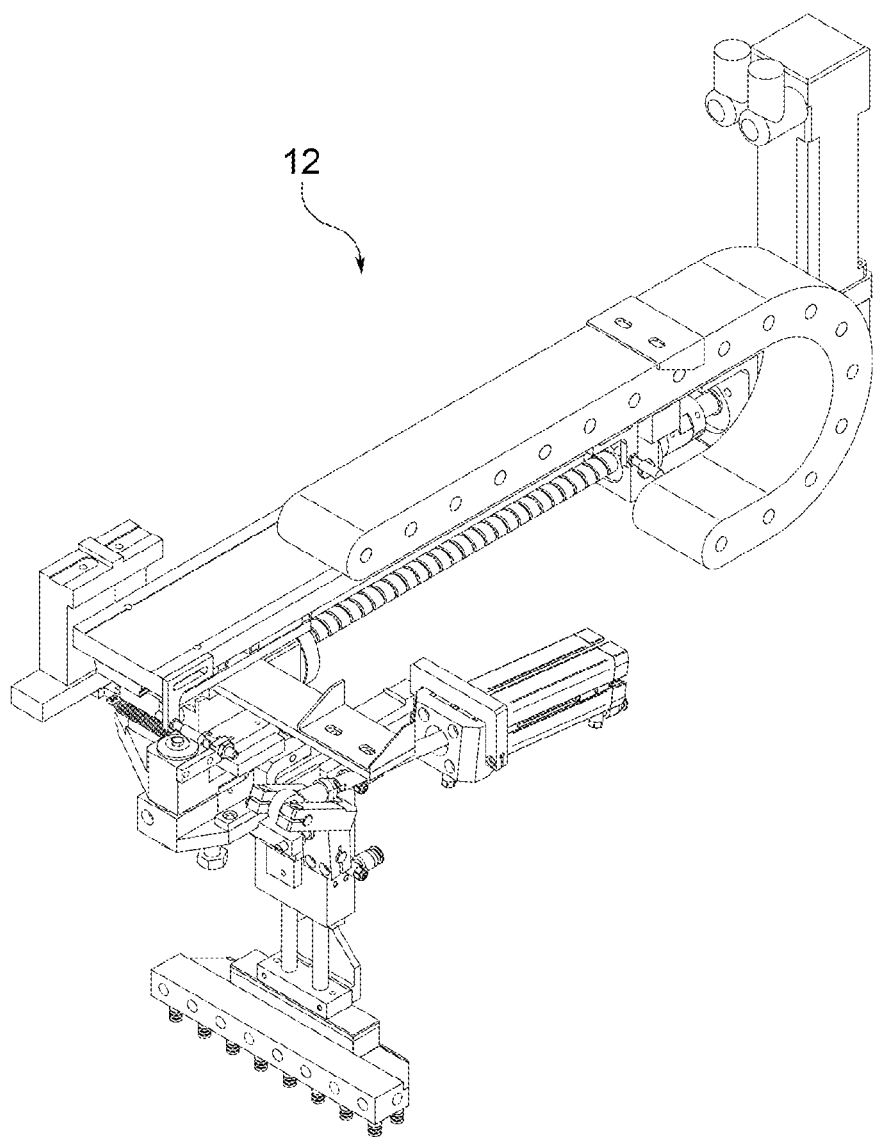
FIG. 7 depicts a perspective view of the enlarged detail VII, shown in FIG. 5.
Figure 8:
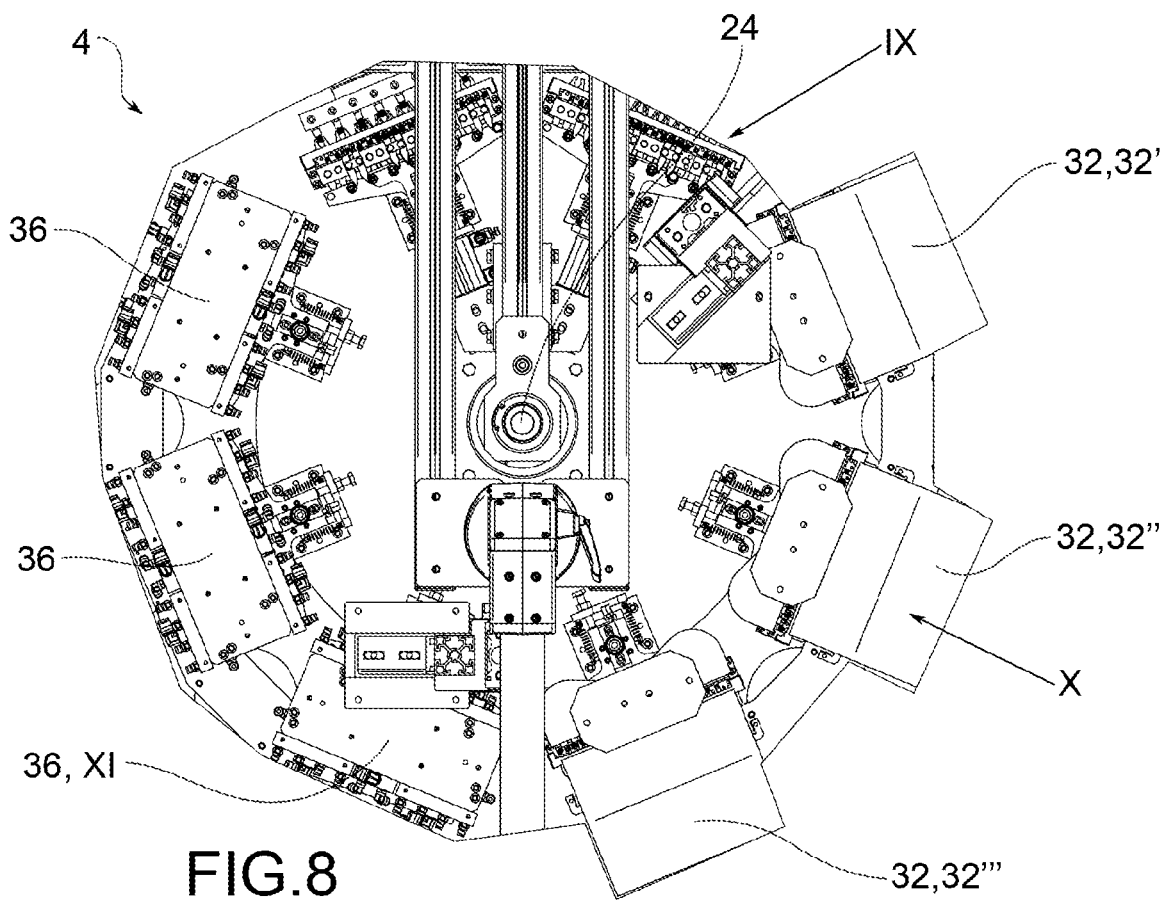
FIG. 8 depicts a partial plan view of the modular unit in accordance with an embodiment of the present invention.
Figure 9:
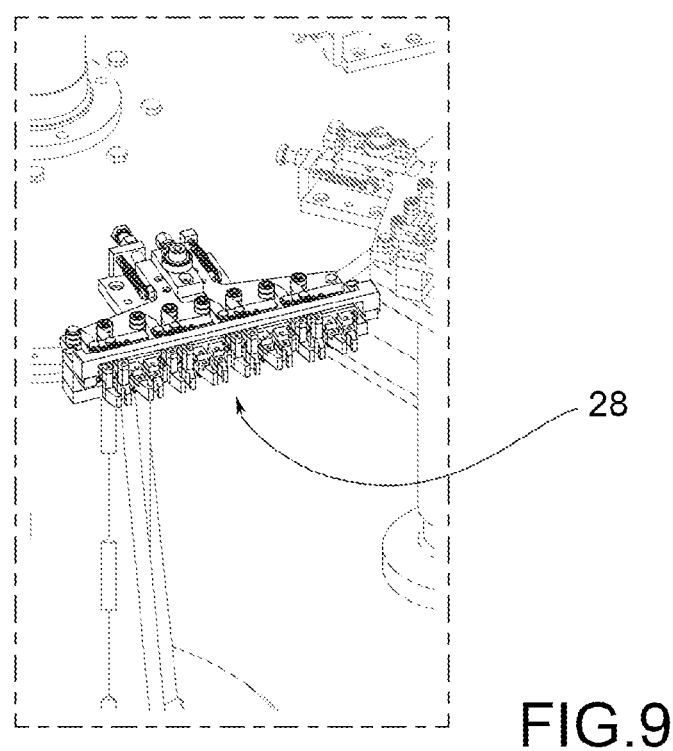
FIG. 9 depicts a perspective view of the enlarged detail IX, shown in FIG. 8.
Figure 10:
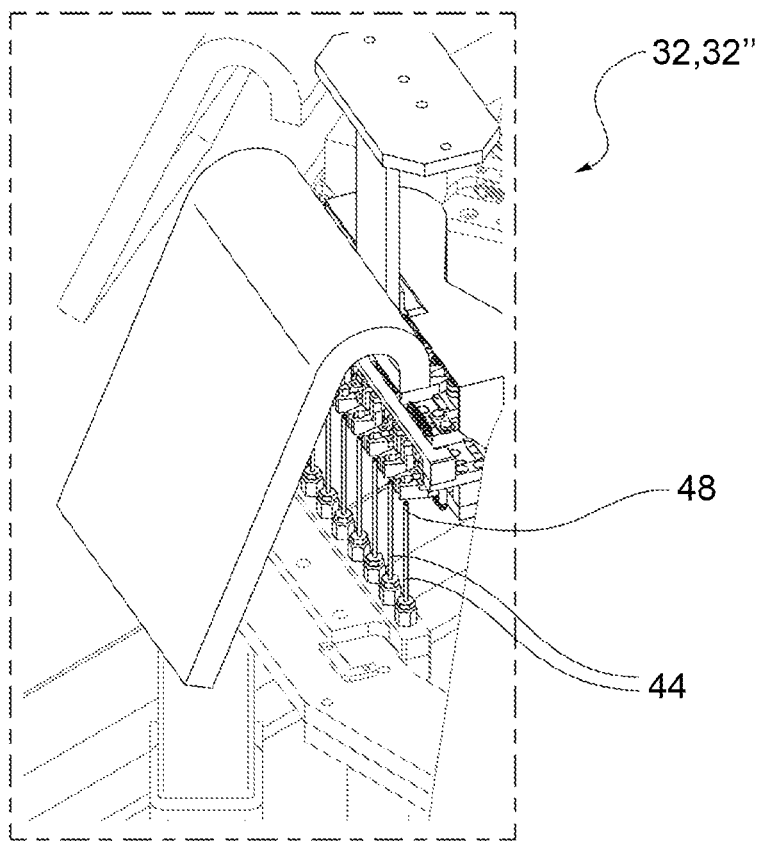
FIG. 10 depicts a perspective view of the enlarged detail X, shown in FIG. 8.
Figure 11:
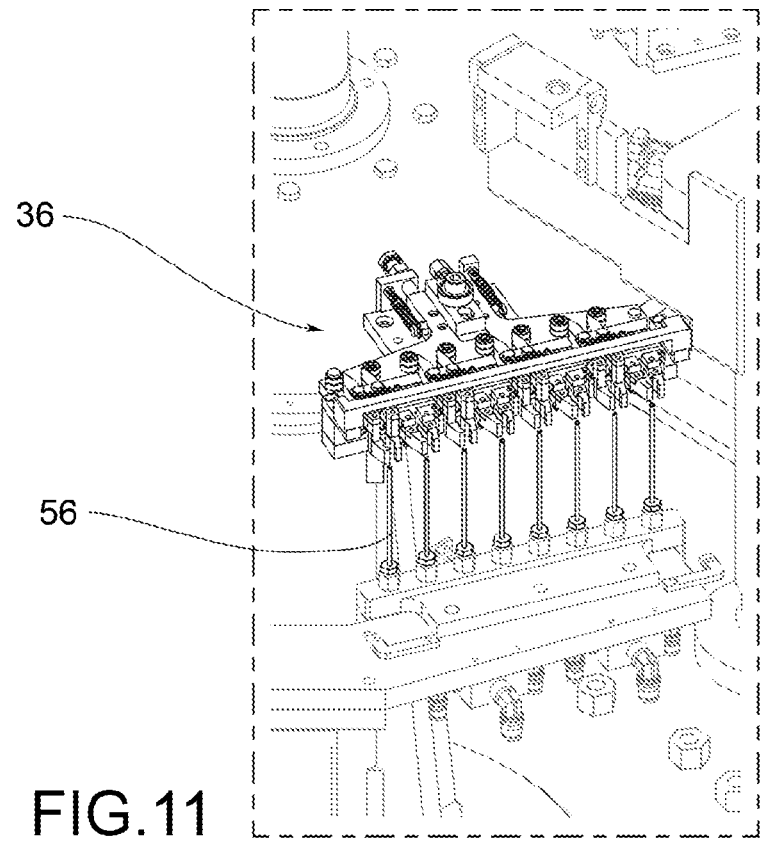
FIG. 11 depicts a perspective view of the enlarged detail XI, shown in FIG. 8.
Figure 13:
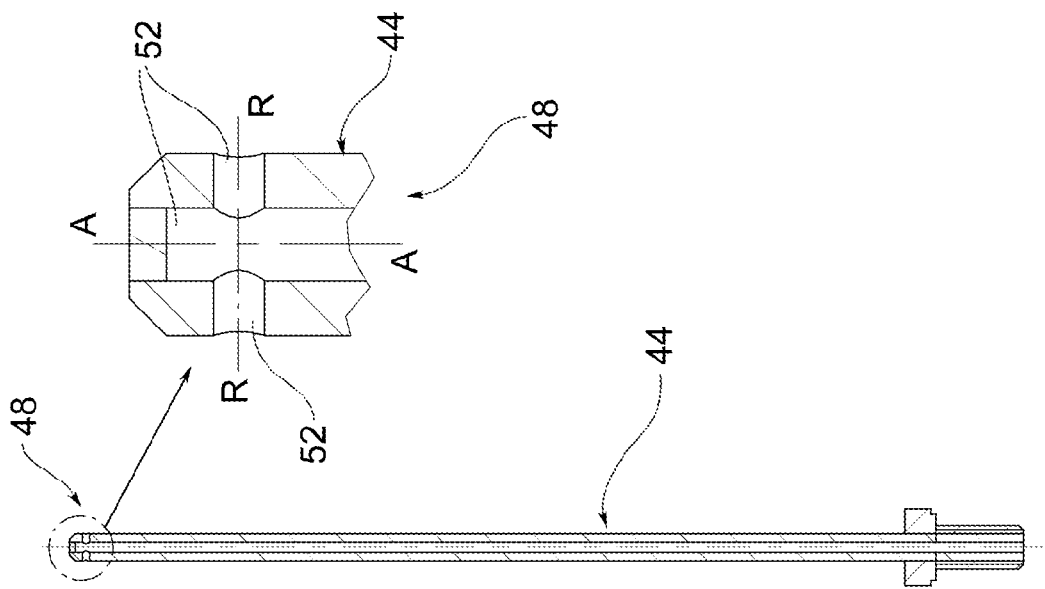
FIG. 13 depicts a side view and a sectional view of a washing nozzle according to the present invention.
Figure 12:
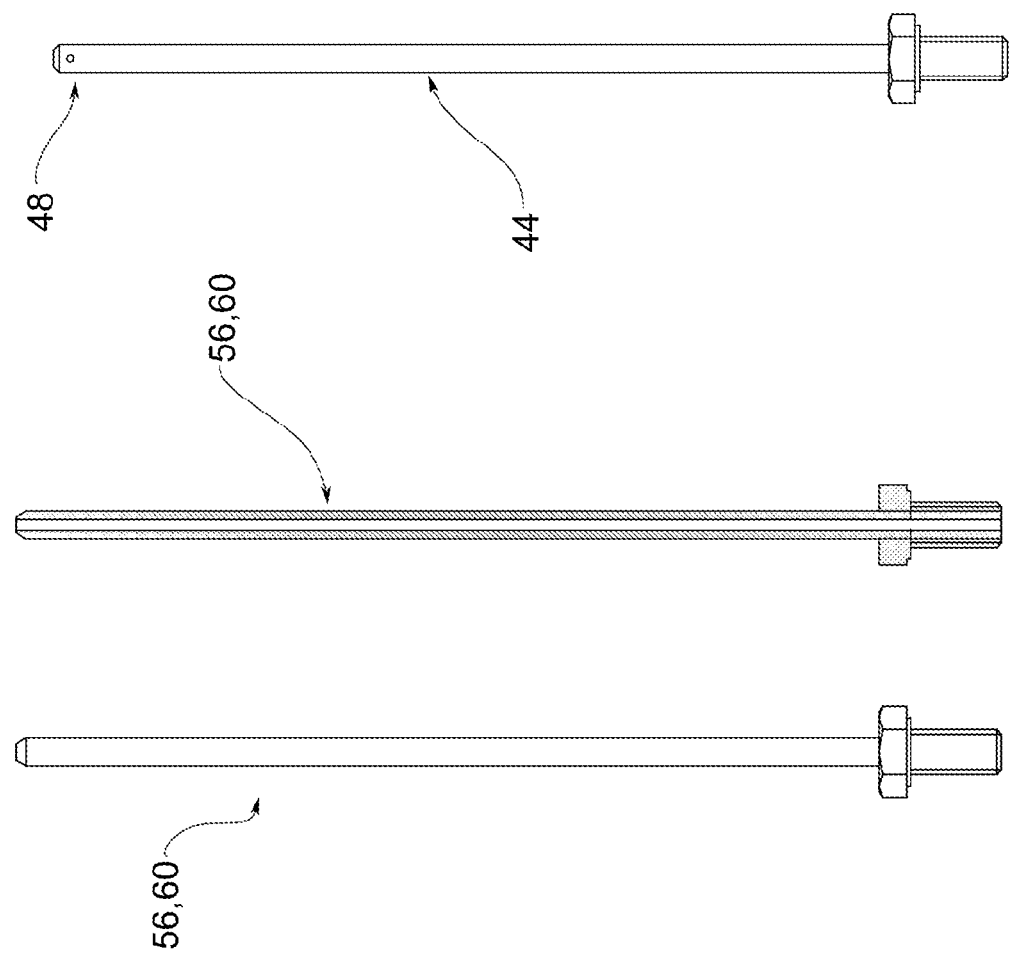
FIG. 12 depicts a side view and a sectional view of a drying nozzle according to the present invention.
Figure 14:
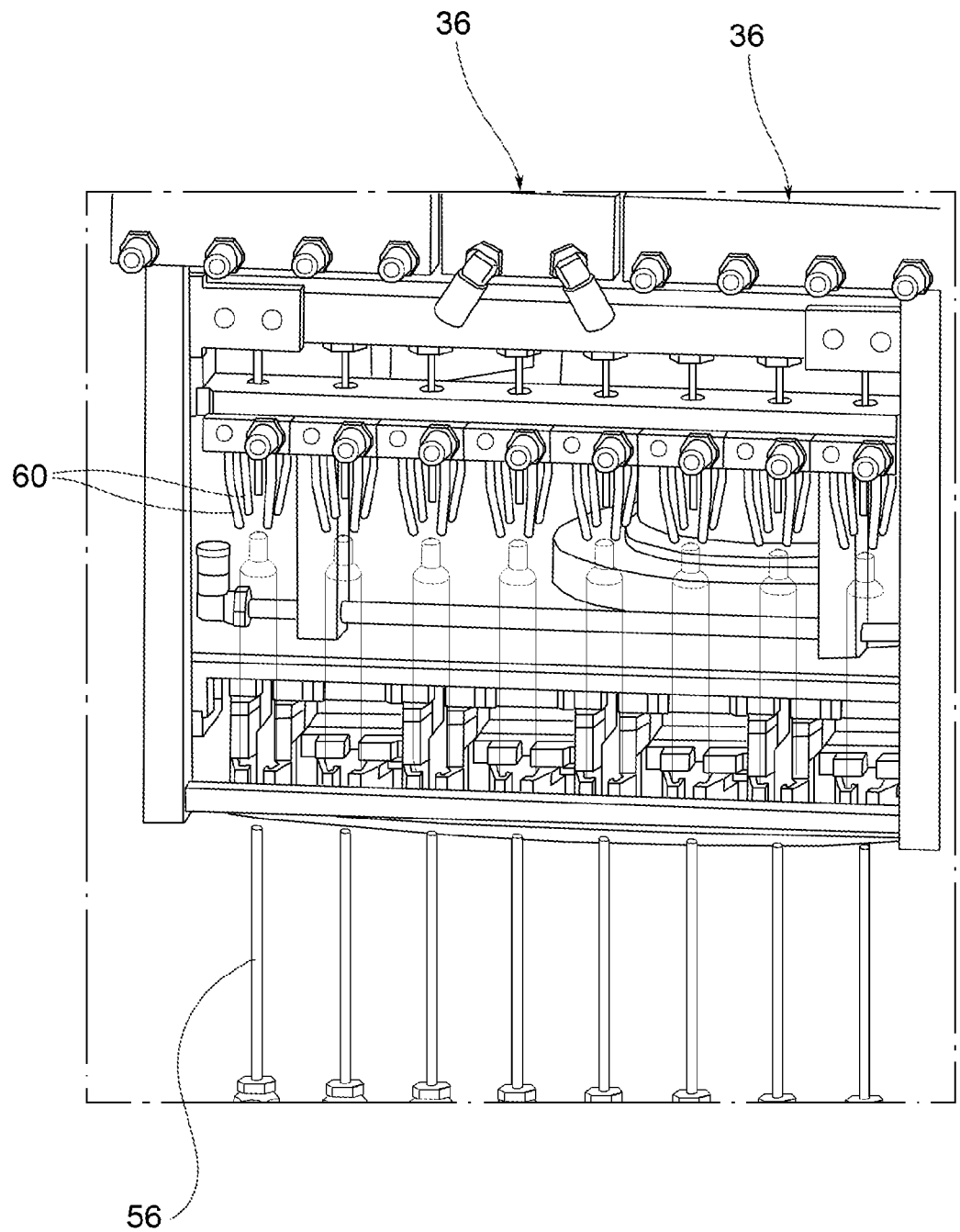
FIG. 14 depicts a partial perspective view of a drying station according to a possible embodiment of the present invention.

Elements or portions of elements in common in the embodiments described below will be indicated by the same numerical references.

DETAILED DESCRIPTION

With reference to the aforesaid figures, a modular unit for washing and drying containers for pharmaceutical use 8 is globally indicated with 4.

The modular unit 4 comprises a load transfer unit 12, configured to take a plurality of containers for pharmaceutical use 8 from an associable input transfer unit 16. Said input transfer unit 16 is typically part of a production line 20 of containers for pharmaceutical use 8.

Thus, the load transfer unit 12 enables the modular unit 4 to interface with the production line 20 from which it takes containers for pharmaceutical use 8.

The modular unit 4 further comprises a washing tower 24 and a group of grippers 28 configured to take said containers for pharmaceutical use 8 from the load transfer unit 12 and to load them onto said washing tower 24.

The modular unit 4 comprises at least one washing station 32, at least one drying station 36 and at least one unloading station 40 for said containers for pharmaceutical use 8.

The washing tower 24, as better described below, is configured to move the containers for pharmaceutical use 8 through said washing stations 32, drying stations 36 and unloading stations 40.

In accordance with a possible embodiment, the washing tower 24 is a device rotatable about at least one axis, for example a vertical axis Y-Y, so as to move the containers for pharmaceutical use 8 through said washing stations 32, drying stations 36 and unloading stations 40.

In order to facilitate the interchange of containers for pharmaceutical use with the washing tower 24, the aforementioned washing stations 32, drying stations 36 and unloading stations 40 are arranged, for example, according to a closed polyline arrangement, and the washing tower 24 is located inside said closed polyline.

In this way, by virtue of the rotation about said axis, the washing tower 24 can move close to each of said washing 32, drying 36 and unloading 40 stations and exchange the containers for pharmaceutical use 8 therewith. The washing tower 24 will thus be surrounded, at least partially, by the washing stations 32, drying stations 36 and unloading stations 40.

The arrangement of the washing stations 32, drying stations 36 and unloading stations 40 according to a closed polyline arrangement, typically according to a circumference or an arc of a circumference, has the advantage of limiting the overall dimensions of the modular unit 4, avoiding to excessively increase the longitudinal extension typical of the production lines 20 of containers for pharmaceutical use 8.

It is also possible to envisage a different arrangement of the washing 32, drying 36 and unloading 40 stations, which can be aligned at least partially according to a longitudinal arrangement.

It is also possible to envisage that the washing tower 24 is provided with roto-translatory or only translatory type movement means so as to move close to each washing station 32, drying station 36 and unloading station 40 and exchange the containers for pharmaceutical use 8 therewith.

According to a possible embodiment, the at least one washing station 32 comprises a plurality of washing nozzles 44 configured to direct a jet of water from the bottom to the top inside the containers for pharmaceutical use 8.

Therefore, said washing nozzles 44 have an elongated configuration so that they can be inserted, at least partially, inside the containers for pharmaceutical use, properly grasped upside down, that is with the open portion facing downwards so as to be able to receive the washing nozzles 44 inside them. Washing in an upside down configuration facilitates the outflow of the washing water after the washing itself.

The washing nozzles 44 are operatively connected to washing water supply means, preferably at a pressure of between 15 bar and 50 bar, preferably between 30 bar and 50 bar.

In accordance with a possible embodiment, the washing nozzles 44 comprise a washing head 48 configured to send a washing jet directed along an axial direction A-A parallel to an extension axis of said washing nozzles 44 and/or along a radial direction R-R perpendicular to said axial direction A-A.

Obviously, it is possible to provide for washing heads 48 configured to spray pressurized water along incident oblique directions with respect to said axial directions A-A and radial directions R-R.

For these purposes, the washing nozzles are provided with suitable dispensing holes 52 close to the washing heads 48. Such dispensing holes 52 can be partially clogged in order to favour washing jets along specific directions.

According to a possible embodiment, the at least one washing station 32 comprises washing water recirculation and filtration means configured to recover the washing water already sent inside the containers for pharmaceutical use 8, filter it appropriately and send it back to the washing nozzles 44.

In accordance with a possible embodiment, the washing tower 24 comprises a plurality of washing stations 32, for example three washing stations 32',32",32''' arranged in series with each other, provided with washing water recirculation and filtration means, such that the washing water is collected and recirculated from the last to the first of the washing stations 32',32",32'''.

More specifically, the recirculation and filtration means are configured to feed the washing stations 32',32" preceding the last washing station 32'''.

In this way, each container is subjected to a washing by each washing station 32 in series, but the first two washing stations 32',32" carry out the washing with recirculated and filtered water, while the last washing station 32''' carries out the washing with clean water, i.e., not recirculated and not filtered. Therefore, the container for pharmaceutical use is subjected to the last washing by the last washing station, e.g., the third washing station 32''', by means of water which is cleaner than the preceding washing carried out by the upstream washing stations 32',32".

In accordance with the invention, the at least one drying station 36 comprises at least one lower drying nozzle 56 configured to direct a flow of air from the bottom to the top inside the containers for pharmaceutical use 8.

Preferably, said lower drying nozzle 56 is provided with movement means for varying its position and allowing it to go closer and/or to be at least partially inserted inside the container for pharmaceutical use 8. Also in the case of drying, preferably the container for pharmaceutical use 8 is grasped in an upside down position so as to allow the at least partial insertion of the lower drying nozzle 56 inside the container and to facilitate the outflow of any residual water therein.

According to the invention, the at least one drying station 36 comprises at least one upper drying nozzle 60 configured to blow air from above for drying the exterior of the container for pharmaceutical use 8, arranged in an upside down position.

Preferably, the drying of the containers for pharmaceutical use 8 is performed by simultaneously actuating both the lower drying nozzles 56 and the upper drying nozzles 60.

In accordance with a possible embodiment, the modular unit comprises a plurality of upper drying nozzles 60 arranged inclined along respective incident straight lines on the side of the containers for pharmaceutical use 8 being placed below.

For example, the upper drying nozzles 60 are arranged symmetrically with respect to the corresponding containers for pharmaceutical use 8 to be dried being placed below.

The unloading station 40 is configured to interface with an associable output transfer unit 64.

Said output transfer unit 64 is typically part of the production line 20 of containers for pharmaceutical use 8. Thus, the output transfer unit 64 allows the modular unit 4 to interface with the production line 20 to which it returns the containers for pharmaceutical use 8, after having washed and dried them.

Preferably, the modular unit 4 for washing and drying containers for pharmaceutical use 8 comprises a programmable processing and control unit so that the washing time and/or the drying time of the containers for pharmaceutical use 8 can be varied. Preferably, each container for pharmaceutical use 8, typically a syringe, remains between 4 and 10 seconds in each washing/drying station; thus in total 12 to 30 seconds per syringe.

In other words, the modular unit 4 is provided with its own programmable processing and control unit so as to be able to vary the washing time and/or the drying time of the containers for pharmaceutical use 8 and so as to adapt it to cooperate with any production line 20 of containers for pharmaceutical use 8.

It is therefore possible to vary the pressures and injection times of the washing water, as well as the drying times, adapting them to containers of different geometry or format, or even different materials or coatings.

In this way, the modular unit 4 is completely autonomous and can be advantageously combined with any existing production line 20.

The operation of the modular unit 4 in accordance with the present invention will now be described.

In particular, moving close to the various washing stations 32, drying stations 36, unloading stations 40 as well as at the input transfer unit 16 and the output transfer unit 64, the washing tower 24 is able to move each container, appropriately taken by the grippers 28 from one station to the other so that the complete washing and drying cycle is carried out.

The container 8 is grasped by the grippers 28 so that it is upside down, i.e., its opening faces downwards.

Therefore, the grippers 28 take the containers for pharmaceutical use 8 from the production line 20 through the input transfer unit 16 and bring them close to the washing stations 32. When the container 8 is brought at the relative washing station 32, while the container 8 remains held suspended by the grippers 28, it is subjected to the washing cycles by the washing nozzles. Then, at the end of the washing cycle carried out by each washing station 32', the container 8 is moved to the adjacent washing station 32" and here it is subjected to a new washing cycle, always remaining suspended and grasped by the grippers 28.

Thus, after the last washing cycle is carried out at the last washing station 32''', the same washing tower 24 carries the same container 8 at at least one drying station 36.

Also in this case, while the container remains held and suspended by the grippers 28, the lower drying nozzles 56 and upper drying nozzles 60 approach the container and perform their respective drying cycles. As seen, the lower drying nozzles 56 insert themselves at least partially inside the container 8 which, as seen, is always held upside down by the grippers 28, while the upper drying nozzles 60 direct their air flows from outside the container and from above.

At the end of the last drying cycle, the washing tower 24 brings the container 8, suitably washed and dried, close to the output transfer unit 64 so that the container 8 can leave the modular unit 4 and return to the production line 20.

As can be seen from the above, the solutions described above allow to overcome the drawbacks of the prior art.

In particular, the present invention provides for a machine for washing and drying medical containers, such as syringes, configured as a modular unit which can be advantageously inserted/disconnected in/from the production line of the same syringes.

Such a solution is particularly versatile and adaptable to any syringe production line, even as a retrofit solution.

The washing unit is arranged in a position such as to allow it to be excluded from the production line if it is not required: also in this case, the solution is particularly versatile in contrast to the solutions of the prior art.

Furthermore, the use and recirculation of the washing water is particularly advantageous: as seen, the washing water is recirculated and/or filtered in order to carry out several washing steps with gradually cleaner water. The washing is then completed in the last washing station with the cleanest, non-recirculated water so as to ensure that the containers for pharmaceutical use are as clean as possible at the end of the last washing station.

Furthermore, the container washing steps are particularly efficient by virtue of the use of high-pressure washing nozzles inserted within the containers from below.

As seen, in order to further optimize such washing, the insertion position of the washing nozzles inside the containers is variable.

Furthermore, the container drying steps are particularly efficient by virtue of the combined use of double drying nozzles both inside, from below, and outside, from above the container.

The washing and drying times are also adjustable in order to ensure the best performance of the modular unit, depending on specific requirements and container formats to be treated.

A person skilled in the art may bring several modifications and variants to the aforementioned solutions for the purpose of meeting contingent and specific needs.

The scope of the invention is defined by the following claims.

The invention claimed is:

1. A modular unit for washing and drying containers for pharmaceutical use comprising:
    a load transfer unit, configured to take a plurality of containers for pharmaceutical use from an associable input transfer unit,
    a washing tower,
    a group of grippers configured to take said containers for pharmaceutical use from the load transfer unit and to load them onto said washing tower,
    at least one washing station, at least one drying station and at least one unloading station for said containers for pharmaceutical use,
    wherein said washing tower is configured to move the containers for pharmaceutical use through said washing stations, drying stations and unloading stations,
    wherein the at least one drying station comprises at least one lower drying nozzle configured to direct a flow of air from the bottom to the top inside the containers for pharmaceutical use and at least one upper drying nozzle configured to blow air from above.

2. The modular unit for washing and drying containers for pharmaceutical use according to claim 1, wherein the washing tower is a device rotatable about at least one axis so as to move the containers for pharmaceutical use through said washing stations drying stations and unloading stations.

3. The modular unit for washing and drying pharmaceutical containers according to claim 1, wherein said washing stations, drying stations and unloading stations are arranged according to a closed polyline arrangement, and wherein the washing tower is located inside said closed polyline.

4. The modular unit for washing and drying containers for pharmaceutical use according to claim 1, wherein the at least one washing station comprises a plurality of washing nozzles configured to direct a jet of water from the bottom to the top inside the containers for pharmaceutical use.

5. The modular unit for washing and drying containers for pharmaceutical use according to claim 4, wherein said washing nozzles comprise a washing head configured to send a washing jet directed along an axial direction parallel to an extension axis of said washing nozzles and/or along a radial direction perpendicular to said axial direction.

6. The modular unit for washing and drying containers for pharmaceutical use according to claim 1, wherein the at least one washing station comprises washing water recirculation and filtration means.

7. The modular unit for washing and drying containers for pharmaceutical use according to claim 1, wherein the washing tower comprises a plurality of washing stations provided with washing water recirculation and filtration means, such that the washing water is collected and recirculated from the last washing station to the first washing station.

8. The modular unit for washing and drying containers for pharmaceutical use according to claim 7, wherein said recirculation and filtration means are configured to feed the washing stations preceding the last washing station.

9. The modular unit for washing and drying containers for pharmaceutical use according to claim 1, wherein said lower drying nozzle is provided with movement means for varying its position and allowing it to go closer and/or to be at least partially inserted inside the container for pharmaceutical use.

10. The modular unit for washing and drying containers for pharmaceutical use according to claim 1, comprising a plurality of upper drying nozzles arranged inclined along respective incident straight lines, on the side of the containers for pharmaceutical use being placed below.

11. The modular unit for washing and drying containers for pharmaceutical use according to claim 10, wherein said upper drying nozzles are arranged symmetrically with respect to the corresponding containers for pharmaceutical use to be dried being placed below.

12. The modular unit for washing and drying containers for pharmaceutical use according to claim 1, wherein said at least one lower drying nozzle and said at least one upper drying nozzles are configured to be actuated simultaneously.

13. The modular unit for washing and drying containers for pharmaceutical use according to claim 1, wherein said unloading station is configured to interface with an associable output transfer unit.

14. The modular unit for washing and drying containers for pharmaceutical use according to claim 1, wherein the modular unit for washing and drying containers for pharmaceutical use comprises a programmable processing and control unit so that the washing time and/or the drying time of the containers for pharmaceutical use can be varied.

15. A production line of containers for pharmaceutical use comprising an input transfer unit and an output transfer unit for said containers for pharmaceutical use, and comprising a modular unit according to claim 1, wherein said modular unit is configured to interface with said input transfer unit and said output transfer unit.

* * * * *